United States Patent [19]
Elfenbein

[11] Patent Number: 4,854,307
[45] Date of Patent: Aug. 8, 1989

[54] APPLYING LIQUID ADHESIVE TO UPPER EYELID TO COUNTERACT DROOPING

[76] Inventor: Bettye Elfenbein, 18041 Biscayne Blvd., #405 Tower 4 South, North Miami Beach, Fla. 33160

[21] Appl. No.: 191,129

[22] Filed: May 6, 1988

[51] Int. Cl.$^4$ .......................... A61H 5/00; A61F 13/12
[52] U.S. Cl. ..................................... 128/76.5; 132/53; 128/163
[58] Field of Search .................... 128/76.5, 25 A, 163; 132/53

[56] References Cited

U.S. PATENT DOCUMENTS

| | | | |
|---|---|---|---|
| 497,052 | 5/1893 | Lamb | 128/76.5 |
| 994,619 | 6/1911 | Taylor | 132/53 |
| 2,079,256 | 5/1937 | Kaiser | 132/53 |
| 2,760,264 | 8/1956 | Javits | 132/53 |
| 2,862,509 | 12/1958 | Porte | 132/53 |
| 3,064,643 | 11/1962 | Dixon | 128/76.5 |
| 3,266,500 | 8/1966 | Weld | 132/53 |
| 3,619,815 | 11/1971 | Towner, Jr. | 132/53 |
| 3,710,788 | 1/1973 | Reeves | 128/76.5 |
| 3,923,044 | 12/1975 | Miller | 128/76.5 |
| 4,653,483 | 3/1987 | Clavin | 128/76.5 |
| 4,677,974 | 7/1987 | Leonardi | 128/76.5 |

FOREIGN PATENT DOCUMENTS

| | | | |
|---|---|---|---|
| 431950 | 7/1926 | Fed. Rep. of Germany | 128/76.5 |
| 644591 | 10/1928 | France | 128/76.5 |
| 43543 | 5/1908 | Switzerland | 128/76.5 |
| 2049 | 2/1879 | United Kingdom | 128/76.5 |

*Primary Examiner*—Edgar S. Burr
*Assistant Examiner*—Tonya Lamb
*Attorney, Agent, or Firm*—Robert M. Schwartz; Edward I. Mates

[57] ABSTRACT

Drooping of an upper eyelid is counteracted by applying a liquid adhesive composition that does not harm the eye along an elongated area where a healthy eyelid would normally fold. Blinking the eye or applying a flexible member to the eyelid along the elongated area of application or applying the adhesive composition to the flexible member and applying the treated member to the outer surface of the droopable eyelid causes the eyelid to fold and the eyelid portions to adhere, thus causing the eyelid to assume an undrooped condition. This invention replaces the need for a surgical procedure to sew the upper eyelid portions together or for a special applicator requiring special training to remove a preformed two-sided tape from a plastic support sheet and apply the removed tape to the outer surface of an unfolded upper eyelid. Instead, this invention provides a simple application procedure that can be performed readily by an untrained individual and apparatus for performing said procedure.

10 Claims, 2 Drawing Sheets

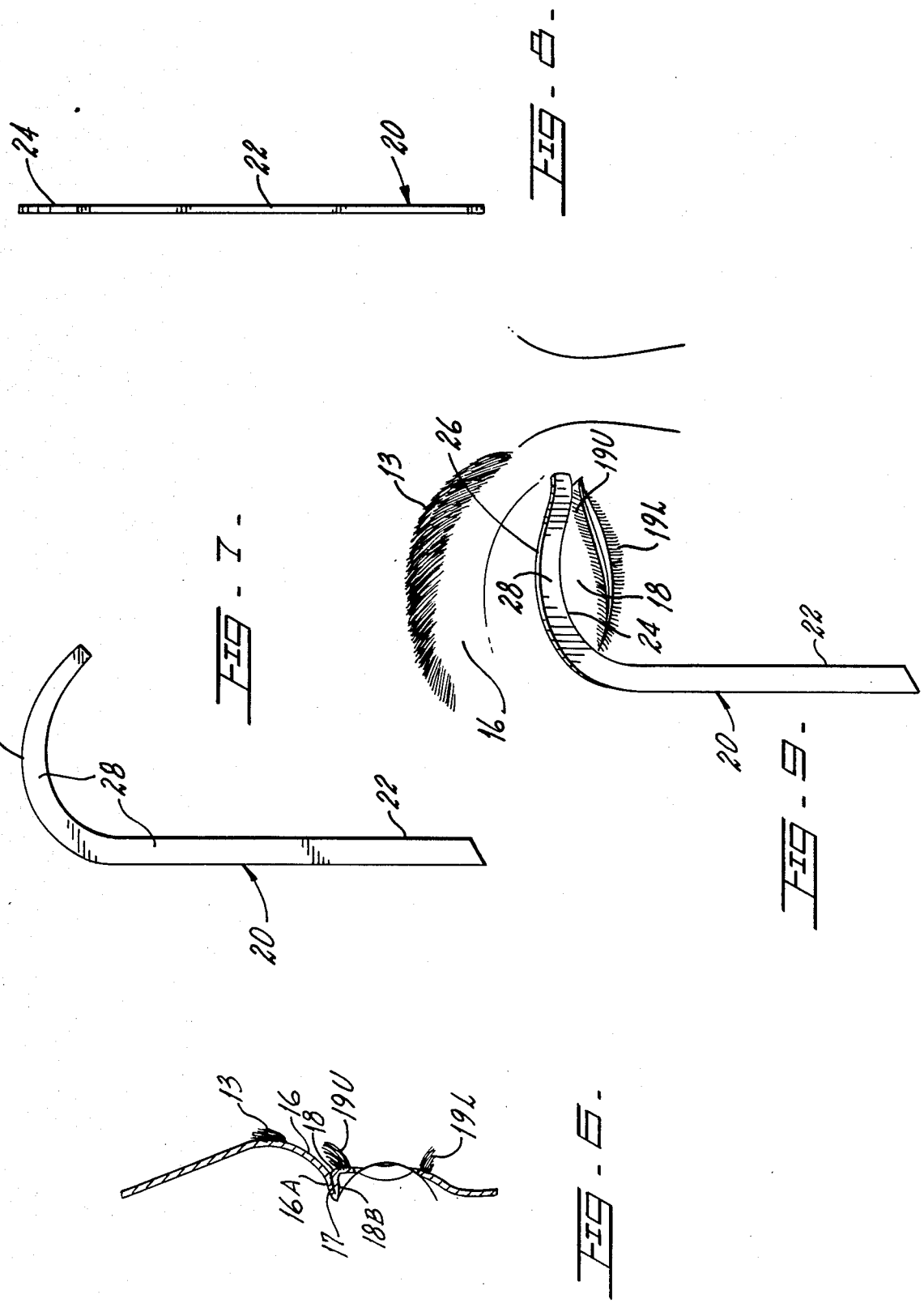

APPLYING LIQUID ADHESIVE TO UPPER EYELID TO COUNTERACT DROOPING

BACKGROUND OF THE INVENTION

This invention relates to the application to an upper eyelid of liquid adhesive material to retain a fold in the skin thereof. This invention replaces either surgical procedures by which the upper and lower portions of an upper eyelid are sewn together or non-surgical procedures such as the application of double faced adhesive tape. Surgical procedures are expensive, scary to a patient and may involve damage to a patient's eyesight. The use of tape to adhere the upper and lower parts of the upper eyelid uses a special instrument which requires special training to remove the double faced tape from a tape storage sheet and to apply the removed adhesive tape onto the outer surface of the upper eyelid.

The upper eyelid moves down over the eyeball when an eye is closed and retracts upwardly over the cornea to expose the iris and pupilary opening when the eye is opened. A thin strip of cartilage known as the tarsal plate holds the skin of the upper eyelid relatively rigid. The skin above the line of rigidity is thin and tends to fold. The skin of the upper eyelid usually sags or droops when a person ages. Such drooping affects the vision above the horizontal line of the tarsal plate as it is impossible to provide a view in an upward direction when the eyeball is rotated upwardly since the line of vision is covered by the drooped portion of the eyelid. Also, the natural puffiness and droop that develops in eyes of people of middle age or older tends to make the person with such drooped eyelids look older. Furthermore, the droop in the upper eyelid can interfere with the application of eye makeup by women.

One method of correcting eye drooping has involved surgery. However, surgical procedures are expensive and dangerous. In the event an eye surgeon accidentally cuts into the eyelid muscle, there is no known surgical procedure for correcting such an accident.

As a substitute for a surgical procedure, the prior art has developed the use of a tape strip member and applicator device. Several tape strip members of desired size and shape are mounted on a thin sheet of plastic and the applicator device is applied to the upper surface of a tape carrying adhesive on opposite side surfaces to first remove the tape strip member from the backing sheet and then applying the removed tape strip member in proper position onto an upper eyelid. It would be desirable to develop a technique avoiding the need for surgery and the need to apply a strip of adhesive tape that supports the upper eyelid in non-drooping relation.

PRIOR ART PATENTS

Several patents have been issued that relate to the application of devices that lift or support the eyelid to avoid drooping. A brief description follows of patents considered most relevant to the present invention:

U.S. Pat. No. 497,052 to Lamb teaches the use of mechanical eyelid lifter and supporter means that is inserted directly between the eyeball and the eyelid. Exposure of the eyeball to a mechanical means may damage the eyeball by scratching.

U.S. Pat. No. 3,064,643 to Dixon shows a scleral brace in the form of a continuous or discontinuous plastic ring that is applied beneath the upper eyelid and outside the eyeball to induce pressure at certain points in the corneo-scleral junction to change the optical power of the eye. This patent does not relate to eliminating drooping of the upper eyelid.

U.S. Pat. No. 3,710,788 to Reeves discloses an adjustable eyelid support movably mounted relative to a bow of a pair of eyeglasses. The glasses must be worn to support the eyelids.

U.S. Pat. No. 3,923,044 to Miller shows a device mounted to an eyeglass frame and having an arm provided with a pad fastened to an eyelid with adhesive. A pacing circuit controls movement of the arm to simulate a normal blinking rate for an eye that is in non-blinking condition.

U.S. Pat. No. 4,653,483 to Clavin shows the application of a two-sided adhesive tape to the skin of an eyelid while the latter is stretched and then folding the skin to attach the latter to the other side of the tape to take a tuck in an eyelid non-surgically. Tapes incorporating an acrylic based pressure sensitive adhesive are disclosed. An applicator requiring special training is needed to apply the tape to the eyelid.

U.S. Pat. No. 4,677,974 to Leonardi shows an eyelid splint comprising a soft resilient pad having a backing attached to two elastic straps that extend around the head of a patient. The free ends of the straps have adjustable interengaging fasteners such as overlapping VELCRO surfaces to adjust the pressure of the pad on the eyelid. This splint replaces cotton pads taped to a patient's face with tincture of benzoin, a flammable adhesive solution, used to augment the adhesiveness of the tape.

Of all the patents previously enumerated, the patent to Clavin is probably most pertinent. However, an adhesive strip tape with adhesive on both major surfaces thereof stored on a sheet of plastic material and covered by a cover sheet, must be first separated from the cover sheet so that the upper adhesive surface of the tape may be exposed to a special tool that removes the tape from the backing sheet. After this difficult step of removing the tape from the backing sheet is accomplished, it is then necessary to apply the tool with the tape bonded thereto onto a proper position over an upper eyelid, where the tape can be transferred to the outer surface of the upper eyelid from its position of adhesion to the tool. This transferring is very difficult to perform, particularly since the adhesiveness of the upper and lower surfaces of the tape must be essentially equal in order to provide sufficient adhesion of the tape to the tool for removal of the tape from the backing sheet onto the tool, an subsequent removal from the tool onto the upper eyelid.

With the difficulty of the prior art, it is obvious that a more efficient method of applying material that does not damage the eye or the eyelid and prevents drooping of the eye is desirable. The present invention provides a method involving the use of liquid adhesive material that does not damage the eye or the eyelid and is more easily applied than the two-sided tape of the prior art. The benefits of the present invention will be understood more readily in the light of a description of a preferred embodiment of the invention that follows.

SUMMARY OF THE INVENTION

The present invention is very helpful in mild cases of blepharo spasm and also avoids drooping of an upper eyelid by applying to a stretched eyelid a liquid adhesive composition that does not harm the eye or the eyelid along a line where a healthy eyelid would normally fold. Blinking the eye or applying a flexible J-shaped member to the eyelid along an elongated, essentially horizontal area of application or applying the adhesive composition to the J-shaped member and applying the treated J-shaped member to the outer surface of the droopable eyelid causes the eyelid to fold along the area of liquid adhesive application. The adhesive sets and causes the folded portions of the upper eyelid to be adhered to one another along the area of application to form two layers of skin that cause the upper eyelid to assume and retain an undrooped condition.

In many cases, the upper and lower portions of the upper eyelid are adhered together by winking the eyelid after applying either a continuous or discontinuous line of adhesive along the natural line about which the healthy eyelid normally folds. A light inward pressure may be applied onto the eyelid against the eyeball using either a person's finger or a special J-shaped flexible member that is pressed to the curvature of the eyeball while applied against the outer surface of the portion of the eyelid that has been treated with the elongated area of adhesive. The application of the elongated area of adhesive raises and tightens the skin of the upper eyelid by creating a new higher fold than the fold that existed previously. The appearance and function of the treated eye improves in seconds. The eye can appear younger and larger. The vertical dimension of the eyelid is reduced to allow greater light entry and an increased field of vision. The application of the adhesive helps correct drooping eyelids and can make asymmetrical eyelids appear symmetrical by the differential application of the adhesive either to one upper eyelid alone or by applying different widths or vertical dimensions of adhesive to the opposite upper eyelids so as to provide a larger folded area for an upper eyelid that droops more than another upper eyelid.

The benefits of this invention will be better understood in the light of a description of a preferred embodiment which follows.

DESCRIPTION OF THE DRAWINGS

In the drawings that form part of a description of a preferred embodiment of this invention.

FIG. 6 shows how the upper eyelid remains folded after the person completes the method of this invention.

FIG. 7 is a plan view of a flexible J-shaped member in the form of a cane that is used to assist in the application of pressure along the elongated area of application of adhesive to cause the upper eyelid to be supported against its eyeball during the last stage of the folding in of the upper eyelid to cause the lower portion of the upper eyelid to be folded against the upper portion of the upper eyelid.

FIG. 8 is an end view of the flexible J-shaped member depicted in FIG. 7; and

FIG. 9 is a view similar to FIG. 4, showing how the flexible J-shaped member of FIGS. 7 and 8 can be used to help refold an upper eyelid when eyelid droop is too pronounced for a person's fingers to refold the upper eyelid.

DESCRIPTION OF PREFERRED EMBODIMENT

Figure 1:
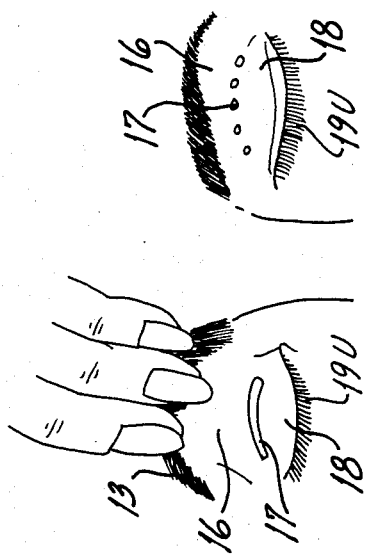
FIG. 1 is a perspective view of the face of a person showing the person unfolding the skin of an upper eyelid preparatory to applying a brush capable of applying a liquid adhesive composition to the outer surface of the unfolded eyelid.
Figure 2:
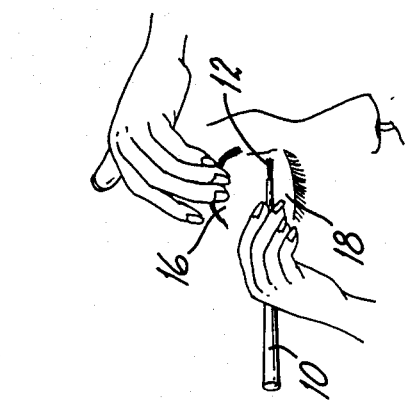
FIG. 2 is an enlarged side view of a portion of the person's face as in FIG. 1 showing the application of a fine brush to the unfolded upper eyelid to apply a liquid adhesive to an elongated area thereof.
Figure 3:
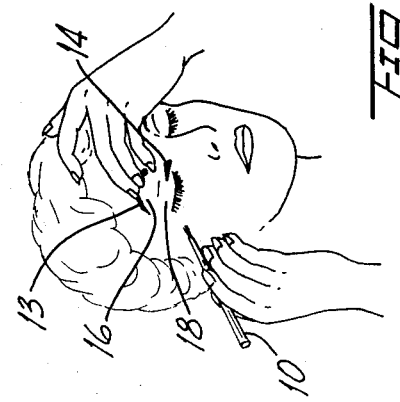
FIG. 3 is an enlarged frontal view of the upper eyelids of a person showing the right eye of the person supported by the fingers to maintain the right upper eyelid open to show the application of liquid adhesive along a substantially horizontal, elongated area of the outer surface of the eyelid and the left eye of the person shown without the fingers applied to indicate a line of dots of liquid adhesive applied along a substantially horizontal, elongated area of the outer surface of the left upper eyelid of the person.

Referring to the drawings, FIG. 1 shows how a person unfolds an upper eyelid 14 by raising the upper portion 16 of the skin of the upper eyelid 14 of his or her right eye toward the right eyebrow 13 and away from its lower portion 18 and its eyelash 19U preparatory to apply adhesive along either a continuous or a discontinuous line of application along the line of normal folding of the upper eyelid. In FIG. 1, the person holds a handle 10 of an applicator brush having fine bristles 12. The brush is stored within a container holding a latex type adhesive, which is the preferable type of liquid adhesive used in a preferred method conforming to the present invention, prior to being brought into the vicinity of the unfolded upper eyelid 14 in the manner depicted in FIG. 1. In FIG. 2, the brush bristles 12 are shown being applied to the unfolded upper eyelid 14 along an essentially horizontal curved elongated area 17 of desired application that corresponds generally to the normal fold line of upper eyelid 14. FIG. 3 shows a curved continuous line of application for the right eye which is one means of applying an elongated area of liquid adhesive. The left eye shows the application of a series of dots of liquid adhesive along the elongated area of normal folding. It is understood that either a continuous line or a series of dots of liquid adhesive may constitute the elongated area of adhesion for both eyes.

Figure 4:
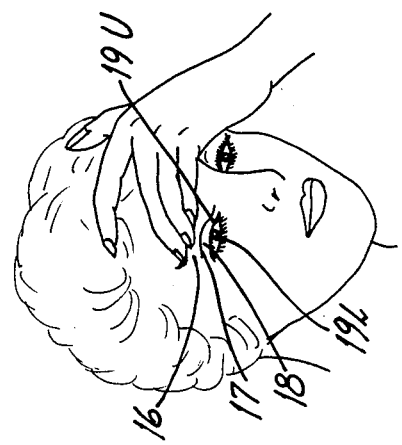
FIG. 4 is a view similar to FIG. 1 taken after the adhesive has been applied to the right eye of the person, fingers of the person's hand used to fold the upper portion of the eyelid over the line or elongated area of application of adhesive.
Figure 5:
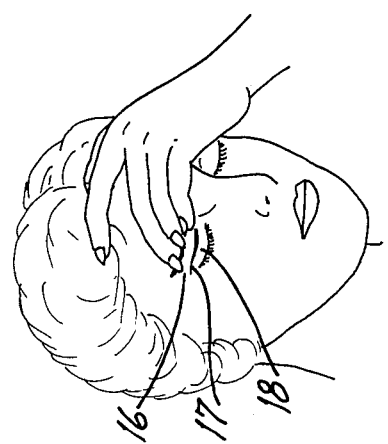
FIG. 5 shows the final step in one method of causing the upper eyelid to adhere in an open position by having the person look up while he holds down the upper portion of the upper eyelid against the line of application of adhesive.

FIGS. 4 and 5 show how a person's fingers may be used to refold the upper eyelid 14 so that the adjacent portions 16A of upper eyelid portion 16 and 18B of lower eyelid portion 18 are folded in superimposed relation with the applied elongated area of liquid adhesive supported therebetween eventually in the arrangement shown in FIG. 6. FIG. 6 also shows the lower eyelash 19L when the eye is open. In FIG. 4, the person looks down while the upper eyelid portion 16 is pushed downward over the elongated area 17 of adhesive and the lower eyelid portion 18. Then, as shown in FIG. 5, the person looks up to raise the lower eyelid portion 18 below upper eyelid portion 16 while the latter is still held down by the person's finger. Thus, adjacent portion 16A of upper eyelid portion 16 forms a layer superimposed and adhesively attached to adjacent portion 18B of lower eyelid portion 18 as depicted in FIG. 6.

Only a few seconds are needed to maintain the eyelid portions 16A and 18B in a secure adhesive arrangement.

In many cases, it is unnecessary to use any tools to insure that folded area 16A of the upper portion 16 of the upper eyelid 14 is adhered in folded relation to folded area 18B of the lower portion 18 of the eyelid. It is merely necessary for the person's fingers to fold the upper portion 16 over the lower portion 18 of the upper eyelids 14 to make the fold. When the person looks up, the eye is seen to be open and the drooping and other factors that cause the reduction of the visible region of the eye vision area is increased over what it would be if the eye were not treated in the manner just depicted.

For some people, it may be necessary to use a little tool to assist in the refolding of the upper eyelid 14. A tool that has been found to be most suitable comprises a flat piece of flexible plastic in the form of a J-shaped member 20 or cane having a straight handle portion 22 and a curved end portion 24. The width of the J-shaped member 20 is about ¼ inch along its major surfaces 28 and the thickness is no more than approximately 1/32 inch along its edge surfaces 26 to enable the flexible J-shaped member to be flexed to follow the curvature of the eyeball immediately beneath the upper eyelid where the curved end portion 24 of flexible J-shaped member 20 is applied flatwise along the line of application of the liquid adhesive. FIG. 9 depicts how the curved end portion 24 follows the curvature of the person's eyeball in one direction and how the flexibility of J-shaped member 20 enables its major surfaces 28 to follow the curvature of the eyeball in an orthogonal direction when applied against the outer surface of upper eyelid 14 in light pressurized engagement thereagainst.

When J-shaped member 20 is used to refold the upper eyelid 14, it is held by handle 22 with curved end portion 24 applied flatwise against the outer surface of upper eyelid 14 and held against the elongated area of liquid adhesive application at a light pressure for a few seconds until the adhesive sets. J-shaped member 20 is then removed from upper eyelid 14 by stripping member 20 in the direction of the person's nose.

It is also possible to use J-shaped member 20 as an applicator for applying the liquid adhesive to upper eyelid 14. In this use, the liquid adhesive is moved from a container by separating the brush from said container, which leaves the liquid adhesive on brush bristles 12. The liquid adhesive is then applied to one major surface 28 of a curved end portion 24 of J-shaped member (depending on which eyelid is to be treated with liquid adhesive). The major surface 28 then coated with liquid adhesive is applied against the outer surface of upper eyelid 14. Since the liquid adhesive adheres more readily to the upper eyelid than to flexible plastic, particularly after setting, only a few seconds are needed to transfer the liquid adhesive from the J-shaped member 20 to the upper eyelid 14.

Many liquid adhesive compositions are available on the market for use in application to the upper eyelid to cause the eyelid to be folded and held in a raised position according to the teachings of this invention. The following preferred composition has been used very successfully.

| COMPOSITION NO. 1 | |
| --- | --- |
| Ingredient | Parts By Volume |
| Water | 30% to 60% |
| Latex | 35% to 95% |
| Hydroxypropyl Methylcelluouse | 0.1% to 3% |
| Carbomer 934 (Thickener) | 0.5% to 3.5% |
| Triethanolamine | 1% to 3% |
| Sodium Benzoate | 0.15% to 0.3% |
| Methylparaben | 0.15% to 0.3% |
| Propylparaben | 0.15% to 0.3% |

The above composition is mixed with a second composition containing 94% by volume of Gum Karaya, a tooth powder adhesive, 0.3% by volume of rose water and the balance distilled water. The mixture has a shelf life of at least three months and is non allergic to human skin or eyes.

In the preferred method of making an adhesive composition, one-half teaspoon of the second composition was mixed with a latex composition such as composition No. 1 containing ⅛ teaspoon of water to ¼ ounce of latex with the other ingredients of composition No. 1 in the ranges specified. The mixture is stored in a cylindrical container into which is inserted an application brush.

When a person wishes to remove the adhesive from an upper eyelid so as to enable the upper eyelid to droop to a comfortable position during sleep, for example, the adhesive can be removed by gentle rubbing of the upper eyelid or by using any commercial liquid eye makeup remover or any other composition of like type. A preferred removal composition for the adhesive remover contains water, propylene glycol, Amphoteric 14, PEG 75, lanolin oil, methylparaben, and F.D. and C. Blue #1. Another suitable composition for removing the adhesive composition is water.

The application of a liquid adhesive composition to a portion of the upper eyelid where adhesion is desired in order to avoid drooping is much more efficient than the application of a two-sided adhesive tape, which is the only known substitute prior to this invention for surgery, to repair the problems of drooping eyelids and the problem of restricted field of vision.

According to the provisions of the patent statutes, the preferred method, mode of operation and chemical composition of materials used in the present invention have been explained and what is now considered to be its best embodiment has been illustrated and described. However, it should be understood, within the scope of the claimed subject matter that follows, the invention may be practiced otherwise than as specifically illustrated and described.

What is claimed is:

1. A method of non-surgically making a tuck or fold in loose foldable skin of an upper eyelid comprising selecting a liquid adhesive that does not harm the eyelid or the eye and is non-allergenic to humans and is not carried by any other member unfolding the upper eyelid to provide a lower portion and an upper portion of the upper eyelid applying to the outer surface of the upper eyelid while unfolded an essentially horizontally extending, elongated area of said liquid adhesive and folding the upper eyelid essentially along the elongated area of application of said adhesive to enable the liquid adhesive to directly adhere the lower portion of the upper eyelid to the upper portion thereof.

2. The method according to claim 1 wherein the liquid adhesive is applied to said elongated area in a continuous essentially horizontal line along the vicinity of the natural fold line of the upper eyelid when said eyelid is unfolded.

3. A method according to claim 1, in which the liquid adhesive is applied to said elongated area in a series of dots along an essentially horizontal line along the vicinity of the natural fold line of the upper eyelid when said eyelid is unfolded.

4. A method as in claim 1 wherein said upper eyelid is refolded along the elongated area of application of said liquid adhesive.

5. A method according to claim 1 wherein said liquid adhesive is an adhesive containing a substantial portion of water and latex.

6. A method according to claim 1 wherein a flexible plastic member having a width on the order of ¼ inch and a thickness not exceeding approximately 1/32 inch is applied over the elongated area of application of said liquid adhesive to assist folding the upper portion of the eyelid and lower portion of the eyelid along the elongated area of application of said liquid adhesive.

7. A method as in claim 1, wherein said liquid adhesive is applied using an applicator brush.

8. A method of folding an upper eyelid comprising providing a flexible member, selecting a latex liquid adhesive, applying latex liquid adhesive to said flexible member, applying said flexible member to the vicinity of the natural fold line of said upper eyelid and pressing the eyelid with said flexible member to fold the unfolded eyelid and removing said flexible member.

9. A method as in claim 8, wherein said flexible member has a relatively wide major surface, relatively narrow edge surfaces, a straight handle portion and a curved end portion, said adhesive applying step comprising applying said liquid adhesive to said wide major surface of said curved end portion, said member applying step comprising applying said curved end portion to said unfolded eyelid with said applied liquid adhesive facing said unfolded eyelid and applying light pressure through said curved end portion to distort said flexible member to conform to the shape of an eyeball covered by said eyelid.

10. A method as in claim 9, wherein said removing step comprises lifting said straight handle portion to gradually lift said curved end portion of said flexible member from said eyelid in the direction of the nose of said individual.

* * * * *